United States Patent [19]

Peter-Hoblyn et al.

[11] Patent Number: 5,266,083
[45] Date of Patent: Nov. 30, 1993

[54] METHOD FOR REDUCING POLLUTION EMISSIONS FROM A DIESEL ENGINE

[75] Inventors: Jeremy D. Peter-Hoblyn, Bodmin, Great Britain; James M. Valentine, Fairfield, Conn.; W. Robert Epperly, New Canaan, Conn.; Barry N. Sprague, Bethlehem, Conn.

[73] Assignee: Platinum Plus, Inc., Stamford, Conn.

[21] Appl. No.: 808,436

[22] Filed: Dec. 16, 1991

Related U.S. Application Data

[63] Continuation-in-part of Ser. No. 794,329, Nov. 12, 1991, abandoned, which is a continuation of Ser. No. 291,245, Dec. 28, 1988, abandoned.

[51] Int. Cl.$^5$ .............................................. C10L 1/30
[52] U.S. Cl. ................................... 44/358; 44/359; 44/361; 44/363; 44/364; 123/1 A
[58] Field of Search .............. 44/358, 359, 361, 363, 44/367; 556/32, 136, 137; 123/1 A, 321, 347

[56] References Cited

U.S. PATENT DOCUMENTS

| | | |
|---|---|---|
| 2,086,775 | 1/1937 | Lyons et al. |
| 2,151,432 | 1/1939 | Lyons et al. |
| 2,875,223 | 2/1959 | Pedersen et al. |
| 3,159,659 | 12/1964 | Pruett et al. |
| 3,328,440 | 6/1967 | Shapiro et al. |
| 3,369,035 | 2/1968 | Schultz |
| 3,397,214 | 8/1968 | Schultz |
| 4,207,078 | 6/1980 | Sweeney et al. |
| 4,225,529 | 9/1980 | Hydes et al. |
| 4,242,099 | 12/1980 | Malec |
| 4,295,816 | 10/1981 | Robinson |
| 4,469,638 | 9/1984 | Bonnemann et al. |
| 4,533,502 | 8/1985 | Rochon et al. |
| 4,568,357 | 2/1986 | Simmon ......................... 44/354 |
| 4,603,215 | 7/1986 | Chandra et al. |
| 4,741,820 | 5/1988 | Couglin et al. |
| 4,787,969 | 11/1988 | Baird, Jr. |
| 4,795,549 | 1/1989 | Couglin et al. |
| 4,891,050 | 1/1990 | Bowers ......................... 44/358 |
| 4,892,562 | 1/1990 | Bowers ......................... 44/324 |
| 5,034,020 | 7/1991 | Epperly ......................... 44/358 |

FOREIGN PATENT DOCUMENTS 2500683 of 0000 Fed. Rep. of Germany .
1948837 4/1970 Fed. Rep. of Germany .

OTHER PUBLICATIONS

Belluco, Organometallic and Coordination Chemistry of Platinu,m Academic Press, N.Y., pp. 221, 222, 226, 232, 295–297, 441–422, 449, 454 & 455 (1974).
Deganello, Transition Metal Complexes of Cyclic Polyolefins, Academic Press, N.Y., pp. 97–100, 102, 277–278, 281–283, 288–291 (1979).
Dickson, Organometallic Chemistry of Rhodium and Iridium, Academic Press, N.Y., pp. 167–169, 178–180, 198–200, 220–226, 248, 258–260, 264, 271 & 277 (1983).
Matilis, The Organic Chemistry of Palladium, Academic Press, N.Y., pp. 68, 70, 76, 77, 83, 93, 102, 103, 136, 158, 165, 202–204, 228, 242, 249, 257–258 (1971).
Chemical Abstracts, 76 112565 p (1972).
Chemical Abstracts, 76 113355 g (1972).
Chemical Abstracts 82 4403z (1975).
Chemical Abstracts 97 110175w (1982).
Chemical Abstracts 97 110181v (1982).

*Primary Examiner*—Margaret Medley
*Attorney, Agent, or Firm*—St. Onge Steward Johnston & Reens

[57] ABSTRACT

The invention presented relates to a method for reducing the emission of nitrogen oxides from a diesel engine without significant loss of fuel efficiency and without significant increases in carbon monoxide and hydrocarbon emissions. The method involves preparing a diesel engine such that the injection timing thereof is set at a point sufficient to obtain reductions in the nitrogen oxides emissions from the engine; and firing the diesel engine with a diesel fuel having admixed therein an additive which comprises a fuel soluble organometallic platinum group metal coordination composition.

12 Claims, No Drawings

METHOD FOR REDUCING POLLUTION EMISSIONS FROM A DIESEL ENGINE

RELATED APPLICATIONS

This application is a continuation-in-part of copending and commonly assigned U.S. patent application having Ser. No. 07/794,329 entitled "Method for Reducing Emissions from or Increasing the Utilizable Energy of Fuel for Powering Internal Combustion Engines", filed in the names of Epperly, Sprague, Kelso, and Bowers on Nov. 12, 1991, now abandoned, which in turn is a continuation of U.S. patent application Ser. No. 07/291,245, filed Dec. 28, 1988, now abandoned, the disclosure of each of which are hereby incorporated by reference.

TECHNICAL FIELD

The present invention relates to a method effective for reducing nitrogen oxides reductions from a diesel engine. The practice of the inventive method permits the reduction of the emission of nitrogen oxides ($NO_x$, where x is an integer, generally 1 or 2) without significantly sacrificing fuel efficiency and without causing a significant increase in the emission of carbon monoxide (CO) and/or unburned hydrocarbons.

BACKGROUND ART

As acknowledged by Needham, Doyle, and Nicol, in "The Low $NO_x$ Truck Engine", Society of Automotive Engineers (SAE), Paper No. 910731, the reduction of nitrogen oxides emissions from diesel engines can be achieved by retarding the injection timing of the engine. Although there is little doubt that such timing changes are effective at reducing $NO_x$ emissions, they carry with them the disadvantage that fuel consumption rates and emission of carbon monoxide and unburned hydrocarbons suffer as a trade-off for the $NO_x$ reductions achieved.

These results are confirmed by the work of Wasser and Perry in "Diesel Engine $NO_x$ Control: Selective Catalytic Reduction and Methanol Emulsion", EPRI/EPA Joint Symposium on Stationary $NO_x$ Control, New Orleans, La., March, 1987. Engine timing modification, therefore, is not a complete answer to the emissions of pollutants such as nitrogen oxides from diesel engines.

The desirability of improving the efficiency of combustion in a vehicle's engine to, inter alia, reduce $NO_x$ emissions, has long been recognized. For instance, Lyons and McKone in U.S. Pat. No. 2,086,775, and again in U.S. Pat. No. 2,151,432, disclose a method for improving combustion efficiency in an internal combustion engine by adding to the fuel what is described as "relatively minute quantities" of catalytic organometallic compounds. The Lyons and McKone patents, though, are directed solely to gasoline-fueled engines and do not address the problem of $NO_x$ emissions from diesel engines.

In a unique application of catalytic technology described in International Publication No. WO 86/03492 and U.S. Pat. No. 4,892,562, Bowers and Sprague teach the preparation of diesel fuel containing fuel soluble platinum group metal compounds at levels of from 0.01 to 1.0 parts per million. Epperly and Sprague disclose a further advance in the field in U.S. Pat. No. 5,034,020.

Moreover, in "Assessment of Diesel Particulate Control—Direct and Catalytic Oxidation", SAE Paper No. 81 0112, 1981, Murphy, Hillenbrand, Trayser, and Wasser have reported that the addition of catalyst metal to diesel fuel can improve the operation of a diesel trap. Among the catalysts disclosed is a platinum compound, albeit one containing chlorine, which is known to reduce the effectiveness of a platinum group metal catalyst.

What is desired therefore, is a system which enables the reduction of $NO_x$ from a diesel engine without the trade-off of reduced fuel consumption and increased emissions of carbon monoxide and unburned hydrocarbons by a process which makes use of a fuel-borne catalyst.

DISCLOSURE OF INVENTION

The present invention comprises a method for reducing emissions from and increasing the combustion efficiency of a diesel engine by preparing the engine such that the injection timing thereof is set at a point effective for reducing nitrogen oxides emissions and applying to the fuel certain platinum group metal compounds which are directly soluble in the diesel fuel. For the purposes of this description, all parts per million figures are on a weight to volume basis, i.e., grams/million cubic centimeters (which can also be expressed as milligrams/liter), and percentages are given by weight, unless otherwise indicated.

DETAILED DESCRIPTION OF THE PREFERRED EMBODIMENT

The method of the present invention relates to the combustion of fuels in diesel engines, by which is meant an engine capable of being run on "diesel fuel" which can itself be defined as fuel oil #2 or #4 petroleum distillates or #6 residual fuel of volatility and cetane number characteristics effective for the purpose of fueling a wide range of internal combustion engines.

In a first aspect of the present invention, the injection timing of the subject diesel engine is set (for instance retarded or set during manufacture of the engine) in a manner designed to reduce the nitrogen oxides emissions from the engine after combustion of a diesel fuel.

It is believed that the closer to top dead center (i.e., point of greatest pressure in the cylinder during the combustion process) at which the timing is set, the greater the reduction of $NO_x$ emissions achieved. However, the injection timing should be set at that level sufficient to reduce nitrogen oxides levels to those desired generally according to either preset arbitrary limits or those required by various regulatory authorities. For instance, in some jurisdictions, it is required that diesel engines (notably new engines) emit no more than 4 grams per brake horsepower-hour (gm/BHP-hr) of nitrogen oxides. Although not always possible, reduction of $NO_x$ levels to no greater than about 4 gm/BHP-hr is, therefore, desired.

Preferably, injection timing can be retarded by between about 0.5° and about 8° to secure the advantages of the present invention. More particularly, the engine timing can be retarded between about 2° and about 6° in order to achieve satisfactory reductions in nitrogen oxides levels without compromising fuel consumption or CO or unburned hydrocarbon emissions to a level beyond that for which at least partial compensation is possible. If, for example, the injection timing is initially set at 18° before top dead center, practice of this invention dictates that it is preferably retarded, by which is meant injection occurs closer in time to top dead center, to about 17.5° to about 10°, more preferably about 16° to about 12°, before top dead center.

The injection timing can be set by retarding the timing of the engine during maintenance or at any other time when access to the engine is possible. In the alternative, the injection timing can be set by having it initially set at the desired level during manufacture or otherwise prior t placing the engine into operation.

A second aspect of the claimed invention involves admixing with the diesel fuel used to fire the diesel engine an additive comprising a diesel fuel soluble organometallic platinum group metal coordination composition, to function as a combustion efficiency enhancer. The additive composition should be temperature stable, and it should be substantially free of phosphorus, arsenic, antimony, or halides. In addition, the additive should have a partition ratio sufficient to maintain significant preferential solubility in the fuel in order to effectively enhance combustion.

The organic nature of the composition provides solubility in diesel fuel thereby facilitating the introduction of the additive into the combustion chamber of a diesel engine. Without such solubility, much of the additive would precipitate in the fuel tank or fuel lines of the diesel engine prior to introduction into its combustion chamber.

The invention identifies temperature stability of the additive as important in practical and operational terms. In a commercial setting, a fuel additive is packaged and then can often sit on a store shelf or in a delivery truck for extended periods of time during which the additive can be exposed to great variations in temperature. If the breakdown temperature of the additive is not sufficiently high (i.e., if the additive is not temperature stable at the temperatures to which it is expected to be exposed), then the packaged additive will quickly break down and become virtually useless.

Moreover, breakdown of the additive after mixing with the fuel will render the additive insoluble in the fuel, since the solubility is provided by the organic functional groups. Such loss of solubility will cause the additive to precipitate and not reach the combustion chamber, as discussed above.

Typically, the breakdown temperature of the additive should be at least about 40° C., preferably at least about 50° C. in order to protect against most temperatures to which it can be expected to be exposed. In some circumstances, it will be necessary that the breakdown temperature be no lower than about 75° C.

In general, the additive comprises the platinum metal group composition as well as a solvent therefor, as will be discussed in more detail below. The organic nature of the platinum group metal composition helps to maintain the composition in solution in the solvent, thereby preventing "plating out" of the platinum group metal composition in the packaging medium.

As noted, the additive of the present invention should be substantially free of objectionable functional groups such as phosphorus, arsenic, antimony, and, especially, halides (i.e., they should not contain a substantial amount of such functional groups) which have significant disadvantages like "poisoning" or otherwise reducing the effectiveness of the platinum group metal composition catalyst. Halides have the additional undesirable effect of rendering a platinum group metal more volatile, leading to reduction of the amount of platinum group metal in the combustion chamber and engine system.

A substantial amount of such functional groups is considered an amount effective to significantly reduce the effectiveness of the catalyst. Preferably, the purified platinum group metal additive composition contains no more than about 500 ppm (on a weight per weight basis) of phosphorus, arsenic, antimony or halides, more preferably no more than about 250 ppm. Most preferably, the additive contains no phosphorus, arsenic, antimony or halides.

Such objectionable functional groups can be minimized in several ways. The platinum group metal composition can be prepared in a process which utilizes precursors or reactant compositions having a minimum of such functional groups; or the additive can be purified after preparation. Many such methods of purification are known to the skilled artisan.

One preferred method of purifying the platinum group metal additive to remove halides is a process utilizing silver salts having non-halide anions which are harmless as compared to the halides being replaced and involves reacting them with the platinum group metal compound, whereby the halides in the composition are replaced by the anion of the silver salt (which can be any silver salts of carboxylic acids, such as silver benzoate, or silver nitrate) and the resulting composition is free of halides, plus a silver halide is produced. For instance, a slurry or solution in a polar solvent such as acetone or an alcohol and water of silver nitrate or silver benzoate can be prepared and reacted with the platinum group metal composition. The resultant platinum group metal composition is a benzoate or nitrate salt with silver halide also being produced. This process can be expected to reduce the halide content of a sample by about 50%, and even up to about 90% and higher.

The relative solubility of the additive in the fuel and water is also important since there is often a substantial amount of water admixed in with fuel. This relative solubility is referred to as the partition ratio and can be expressed as the ratio of the amount in milligrams per liter of composition which is present in the fuel to the amount which is present in the water. This can most easily be determined in a 100 milliliter (ml) sample which is 90% fuel and 10% water. By determining the amount of composition in the fuel and the amount in the water, the partition ratio can be readily determined. The preferential solubility of the additive in fuel as compared to water can be critical because if a substantial amount of the additive is dissolved in the water which may be present, the overall effectiveness of the additive is proportionally reduced. This partition ratio should be at least about 25 and is most preferably greater than about 50.

In order to reduce the water susceptibility of the platinum group metal composition, it is desired that the composition have at least one platinum group metal-to-carbon covalent bond. A platinum group metal-to-oxygen or platinum group metal-to-nitrogen bond can be acceptable, but there must also be at least one metal to carbon bond.

Platinum group metals include platinum, palladium, rhodium, ruthenium, osmium, and iridium. Compounds including platinum, palladium, and rhodium, especially compounds of platinum alone or possibly in combination with rhodium compounds are preferred in the practice of this invention since the vapor pressure of these metals is sufficiently high to form engine deposits which have the desired effect on combustion.

Specific suitable compounds according to the present invention include those platinum metal group-containing compositions selected from the group consisting of a) a composition of the general formula

$$L^1MR^2$$

wherein $L^1$ is either a single cyclic polyolefin or nitrogenous bidentate ligand or a pair of nitrogenous or acetylenic monodentate ligands; M is a platinum group metal, especially platinum itself; and $R^1$ and $R^2$ are each, independently, substituted or unsubstituted alkyl (e.g., 1-5 carbons), benzyl, nitrobenzyl, aryl, cyclopentadiene or pentamethyl cyclopentadiene, preferably benzyl, methyl or phenyl;

b) a composition of the general formula

$$L^2M^1R^3$$

wherein $L^2$ is either a single cyclic polyolefin or nitrogenous bidentate ligand or a pair of nitrogenous or acetylenic monodentate ligands; $M^1$ is rhodium or iridium; and $R^3$ is cyclopentadiene or pentamethyl cyclopentadiene;

c) a composition of the general formula

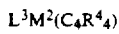
$$L^3M^2(C_4R^4_4)$$

wherein $L^3$ is either a single cyclic polyolefin or nitrogenous bidentate ligand or a pair of nitrogenous monodentate ligands; $M^2$ is platinum, palladium, rhodium, or iridium; and $R^4$ is $COOR^5$, wherein $R^5$ is hydrogen or alkyl having from 1 to 10 carbons, preferably methyl;

d) a composition of the general formula

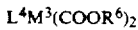
$$L^4M^3(COOR^6)_2$$

or a dimer thereof, wherein $L^4$ is a non-nitrogenous cyclic polyolefin ligand, preferably cyclooctadiene or pentamethyl cyclopentadiene; $M^3$ is platinum or iridium; and $R^6$ is benzyl, aryl, or alkyl, preferably having 4 or more carbons, most preferably phenyl;

e) a composition comprising the reaction product of $[L^5RhX]_2$ and $R^7MgX$ wherein $L^5$ is a non-nitrogenous cyclic polyolefin ligand, preferably cyclooctadiene or pentamethyl cyclopentadiene; $R^7$ is methyl, benzyl, aryl, cyclopentadiene or pentamethyl cyclopentadiene, preferably benzyl or phenyl, and X is a halide. Although presently uncharacterized, it is believed that this reaction product assumes the formula $L^5RhR^7$.

Functional groups which are especially preferred for use as ligands $L^1$ through $L^3$ are neutral bidentate ligands such as cyclopentadiene, cyclooctadiene, pentamethyl cyclopentadiene, cyclooctatetrene, norbornadiene, o-toluidine, o-phenantholine, and bipyridine. Most preferred among monodenate ligands is pyridine.

Also useful in the present invention are f) palladium acetylene complexes having the general formula

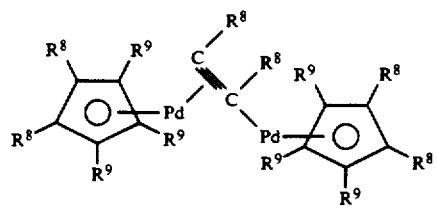

wherein $R^8$ is aryl or alkyl; and $R^9$ is aryl;

g) metal allyl complexes having the general formula

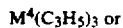
$$M^4(C_3H_5)_3 \text{ or}$$

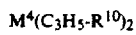
$$M^4(C_3H_5\text{-}R^{10})_2$$

wherein $M^4$ is a platinum group metal, especially rhodium or iridium; and $R^{10}$ is hydrogen, aryl, or alkyl;

h) platinum (IV) compositions having the general formula

$$R^{11}_3PtR^{12}$$

wherein $R^{11}$ is aryl, alkyl or mixtures thereof; and $R^{12}$ is hydroxyl (—OH), acetylacetonate (—CH$_3$.(COCH$_3$)$_2$), cyclopentadiene or pentamethyl cyclopentadiene (exemplary of which is trimethyl platinum hydroxide); and i) a composition of the general formula

$$L^6M^5R^{13}$$

wherein $L^6$ is substituted or unsubstituted butadiene or cyclohexadiene; $M^5$ is rhodium or iridium; and $R^{13}$ is cyclopentadiene or pentamethyl cyclopentadiene (exemplary of which are butadiene rhodium cyclopentadiene and butadiene iridium cyclopentadiene.

The synthesis of the preferred compounds is relatively straightforward, with the most care being taken to avoid "contamination" of the product by the objectionable functional groups discussed above. For instance, the most preferred synthetic route for production of the compounds of the formula $L^1PtR^1R^2$ is by reacting commercially available platinum halides with the desired neutral ligand (except the pyridine derivative which can be added by displacement after the fact) and then reacting with a Grignard reagent having the formula $R_2MgX$, where X is a halide (and where the desired $R^1$ and $R^2$ in the end product are the same functional group). Where the $R^1$ and $R^2$ functional groups are desired to be different, a straightforward substitution reaction can then be run.

Exemplary of compounds suitable for use in the present invention and prepared in this manner are dipyridine platinum dibenzyl; bipyridine platinum dibenzyl; dipyridine palladium diethyl; cyclooctadiene platinum dimethyl; cyclooctadiene platinum diphenyl; cyclooctadiene platinum dibenzyl; cyclooctadiene platinum dinitrobenzyl; cyclooctadiene platinum methyl cyclopentadiene; norbornadiene platinum dicyclopentadiene; dimethyl platinum cyclooctatetrene (which often assumes the formula dimethyl platinum cyclooctatetrene platinum dimethyl); and cyclooctadiene osmium bis (cyclopentadiene).

The compounds of the formula $L^2M^1R^3$ are prepared along a similar pathway, as are the reaction products of $[L^5RhX]_2$ and $R^6MgX$, with the exception that the starting materials have only one R functional group and are, with respect to $L^2M^1R^3$, $L^2RhR^3$ or $L^2IrR^3$. Exemplary of suitable compounds of the formula $L^2M^1R^3$ are cyclooctadiene rhodium cyclopentadiene; cyclooctadiene rhodium pentamethyl cyclopentadiene; norbornadiene rhodium pentamethyl cyclopentadiene; cyclooctadiene iridium cyclopentadiene; cyclooctadiene iridium pentamethyl cyclopentadiene; norbornadiene iridium cyclopentadiene; and norbornadiene iridium pentamethyl cyclopentadiene. Exemplary of compounds which can function as the precursors for the reaction product can include cyclooctadiene rhodium chloride dimer and benzyl magnesium chloride.

Advantageously, in the Grignard-type syntheses, the Grignard reagent can be replaced by one having the formula $R_2Z$ where Z is commonly Na, Li, K, or Tl. This is especially preferred since the halides which are present in a Grignard reagent are eliminated, providing less halides in the final product and also advantageously producing a higher yield of the desired product.

The preparation of compositions of the formula $L^3M^2(C_4R^4_4)$ is also straightforward and proceeds by reacting $M^2$(dibenyilidine acetone)$_2$ with dimethylacetylene dicarboxylate in acetone and then adding the $L^3$ ligand. Exemplary of suitable compounds according this formula, which has the structure

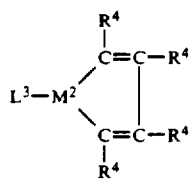

is tetrakis (methoxy carbonyl) palladia cyclopentadiene (wherein $L^3$ is cyclopentadiene, $M^2$ is palladium, and $R^4$ is $COOH_3$).

The compositions of the formula $L^4M^3(COOR^5)_2$ can be prepared by reacting $L^4M^3X_2$, where X is a halide and a silver carboxylate such as silver benzoate. This composition can form a dimer, especially when $M^3$ is platinum. Exemplary of suitable compounds having the general formula $L^4M^3(COOR^5)_2$ are cyclooctadiene platinum dibenzoate dimer; and pentamethyl cyclopentadiene iridium dibenzoate.

The most preferred synthetic route for production of the noted acetylene compounds is by reacting the trimeric palladium salt of a carboxylic acid $([Pd(OOCR^6)_2]_3)$, where $R^6$ is alkyl such as methyl or ethyl, or aryl such as phenyl, such as palladium acetate, propionate or benzoate, with a substituted acetylene, such as diphenylacetylene or methylphenylacetylene, in the presence of a polar solvent, such as an alcohol like methanol ($CH_3OH$). For example, when the reactants are palladium acetate and diphenylacetylene, the product is u-diphenylacetylene bis($^5$ pentaphenyl cyclopentadiene) dipalladium, which has the general formula

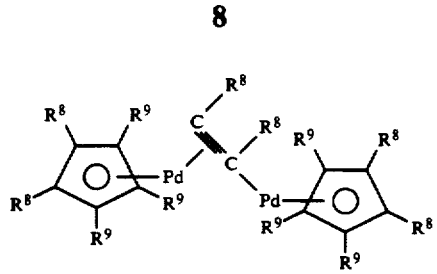

where $R^8$ and $R^9$ are each phenyl.

The disclosed metal allyl compositions can be prepared by reacting commercially available rhodium or iridium halides, such as $RhCl_3$ or $IrCl_3$, with an allyl Grignard reagent, such as $C_3H_5MgBr$, in a 3:1 molar ratio to produce the desired metal allyl, such as bis (phenyl allyl) palladium, and MgBrCl.

The platinum (IV) compositions can be prepared, for instance, by reacting $R_3^{11}PtX$, where $R^{11}$ is aryl or alkyl, such as phenyl, benzyl or methyl or mixtures and X is a halide, with $NaR^{12}$, where $R^{12}$ is cyclopentadiene or pentamethyl cyclopentadiene.

Reaction of the $R_3^{11}PtX$ complex with aqueous acetone solutions containing a silver compound such as $Ag_2O$ results in a product where $R^{12}$ is hydroxyl. Alternatively, treatment of the $R_3^{11}PtX$ complex with a solution of acetylacetone in alcoholic potassium hydroxide results in a product where $R^{12}$ is acetyl acetonate.

The compounds of the formula $L^6M^5R^{13}$ can be prepared by reacting commercially available metal halides with butadiene and cyclohexadienes and then reacting with a Grignard reagent having the formula $R_{13}MgX$, where X is a halide.

The additives when added to diesel fuel and supplied to an engine are believed to reduce the so-called "delay period" which occurs immediately after injection of the fuel into the combustion chamber is initiated, due to improvement in the shape of the indicator diagram. This reduction of delay between vaporization and ignition can explain the improvements noted by the present invention but not suggested by the prior art; however, this theoretical explanation is presented only because it is the best available and there may well be others which even better explain the surprising results noted. The additives provide beneficial results over long periods of continuous use in internal combustion diesel engines.

Timing of fuel injection during the compression stroke is an important consideration in a diesel engine. The inventive fuel additive is believed to reduce the delay time until fuel starts to burn. Accordingly, its effect mimics advancing the time of fuel injection before top dead center. As a result, retarding fuel injection timing (i.e., delaying injection) while utilizing the noted additive can optimize the overall system (improve fuel economy while meeting emission standards).

The additive will be added to the fuel in an amount effective to improve engine performance, especially in terms of recovering fuel efficiency sacrificed by retarding engine timing in order to reduce nitrogen oxides as well as in emissions reduction. Typically, the platinum group metal compound will supply an amount of the platinum group metal within a range of about 0.01 to 1.0 parts of the platinum group metal per one million parts of fuel (ppm w/v). A more preferred range is from about 0.05 to 0.5 ppm and, most preferably, the platinum group metal will be supplied at a level of from about 0.10 to 0.30 ppm on the same basis.

The additive composition will preferably include a solvent which is soluble in the fuel, preferably octyl nitrate. The fuel additive compositions may also contain other additives, such as detergents, antioxidants and cetane improvers which are known as beneficial to engine performance, but the use of such is not an essential feature of the invention.

The total amount of solvent and other additives used will depend on the dosage of platinum group metal composition required and on what is a convenient concentration to handle relative to the amount of fuel to be treated. Typically, solvent (plus other like additive) volumes of about 0.1 to about 40.0 liters/gram of platinum are acceptable.

It has surprisingly been found that the use of the platinum group metal additives discussed above will substantially overcome the disadvantages of retarding injection timing to achieve $NO_x$ reductions. In other words, the use of the noted additives can increase fuel efficiency (i.e., reduce fuel consumption) to levels observed before the retarding of the injection timing to achieve $NO_x$ reductions. Furthermore, emissions of carbon monoxide and unburned hydrocarbons caused by retarding the injection timing may also be reduced. In order to achieve further reductions in CO and unburned hydrocarbons, a suitable oxidizer, such as a bed of extrudate or pellets of alumina or other refractory oxide, or a monolith having a surface of a refractory oxide or a metal matrix, can also be utilized. In this way, significant reductions in nitrogen oxides are obtained without the art accepted tradeoffs associated therewith.

In addition, if the increase in particulates caused by retarding the timing of the diesel engine is to an undesirable level, a diesel engine particulate trap can be employed. In fact, the use of the additives described above can also have an advantageous impact on the operation of a diesel trap, as detailed in copending and commonly assigned U.S. patent application having Ser. No. 07/808,435, entitled "Method For Reducing The Particulate Emissions From A Diesel Engine", filed in the names of Peter-Hoblyn, Valentine, Epperly, and Sprague on even date herewith.

In this aspect of the present invention, a diesel engine is provided having associated therewith a diesel engine particulate trap. By this is meant a diesel engine particulate trap is disposed such that the exhaust stream from the engine passes therethrough. Generally, a diesel engine particulate trap is disposed on the tailpipe of the vehicle in which the diesel engine is located, downstream from the exhaust manifold.

Suitable diesel traps are known to the skilled artisan and generally comprise an apparatus designed to trap or collect particulates which are present in the exhaust stream of the diesel engine. Such a trap can be made of any suitable material such as a ceramic (for instance, a cordierite ceramic material), glass fibers, or metals.

Since flow resistance to the exhaust increases in proportion to the efficiency of the diesel trap at collecting particulates, a compromise must be made between trap efficiency and exhaust back pressure. One type of diesel engine particulate trap which is found to be effective at trapping particulates while still an acceptable compromise in terms of back pressure created are traps available under the tradenames Dieselfilter or EX 51 100/17 from Corning Glass Corporation of Corning, N.Y.

More specifically, a suitable diesel engine particulate trap consists of a gas permeable material, such as a ceramic. The trap is formed such that it has at least two (and generally several parallel gas channels longitudinally arranged in a honeycomb-type structure extending between what can be referred to as an upstream, or engine-side, face and a downstream, or exhaust-side, face. Each passage is plugged at one of its faces such that alternate faces of adjacent passages are plugged. In this way, exhaust entering the trap through a passage at its unplugged upstream face, must pass through a wall into an adjacent passage in order to exit the trap from its unplugged downstream face. Particulates in the exhaust are then trapped or collected on the wall. Such a trap is described, for instance, in U.S. Pat. No. 4,568,357 to Simon, the disclosure of which is incorporated herein by reference.

The particulate trap used in the method of the present invention can be one which is self regenerating, that is, trapped particulates are ignited by heat derived from the engine, usually from the hot exhaust gasses themselves. Unfortunately, a four-cycle engine only sometimes provides sufficient exhaust heat to regenerate the trap, whereas two-cycle engines rarely provide sufficient heat.

Another type of trap arrangement which can be used involves the use of a Donaldson trap which involves the addition of an auxiliary heating coil used to bring the trap particulates to ignition by triggering ignition at programmed times in the engine operation cycle. As discussed above, although a Donaldson trap can be effective at regenerating a particulate trap, the expenditure of energy makes the use of a Donaldson trap inefficient.

In order to heat the particulates collected on the trap to their ignition-temperature, a glow plug or auxiliary burner can be provided, advantageously in contact with the upstream face of the trap. The glow plug or burner can be activated intermittently, such as in response to back pressure increase, elapsed time, or other suitable parameters to ignite the particulates. The use of such means is similarly inefficient.

Often, when heat assisted traps are employed, a two trap system is utilized. In such a system, two particulate traps are arranged in parallel. After a specified period of engine operation during which the exhaust is passed through one of the traps, such as between 1 and 2 hours, the system shifts so that the exhaust is passed through the other. During its period of inactivity, regeneration of the inactive trap can occur.

When the additive of this invention is admixed with the diesel fuel used to fire the diesel engine, it functions as an ignition temperature reducer. The additive can also function to replenish catalyst metal coated on the trap surfaces.

It has suprisingly been found that the use of the platinum group metal additives discussed above will reduce the ignition temperature of the trapped particulates to a level whereby self-regeneration of a particulate trap, especially in a four-cycle diesel engine may occur. Even if self-regeneration cannot completely occur, i.e., in a four-cycle engine which is not operating hot enough or in a two-cycle engine, the use of the described additives will reduce the temperature to which an auxiliary heat source is required to raise the diesel engine particulate trap, thereby increasing the efficiency of the use of the auxiliary heat source. In this way, significant improvements in the use of a diesel engine particulate trap are obtained, without the art accepted tradeoff of substantially increased back pressure caused by clogging of the trap by collected particulates.

Even when not sufficiently efficient to offset entirely the increase in particulates observed when injection timing is retarded, a diesel trap can help to at least partially eliminate the particulates generated by retarding the injection timing. Moreover, the additive can also decrease the ignition temperature of particulates collected on the trap. This can facilitate regeneration of the trap for greater efficiency.

The above description is for the purpose of teaching the person of ordinary skill in the art how to practice the present invention, and it is not intended to detail all of those obvious modifications and variations of it which will become apparent to the skilled worker upon reading the description. It is intended, however, that all such obvious modifications and variations be included within the scope of the present invention which is defined by the following claims.

We claim:

1. A method for increasing the combustion efficiency of a diesel engine comprising
   a) preparing a diesel engine such that the injection timing thereof is set before top dead center at a level sufficient to obtain reductions in the nitrogen oxides emissions from the engine; and
   b) firing the diesel engine with a diesel fuel having admixed therein an additive which comprises a fuel soluble organometallic platinum group metal coordination composition selected from the group consisting of
   i) a composition of the general formula

   $L^1 PtR^1 R^2$ wherein $L^1$ is either a single cyclic polyolefin or nitrogenous bidentate ligand or a pair of nitrogenous or acetylenic monodentate ligands; and $R^1$ and $R^2$ are each, independently, substituted or unsubstituted methyl, benzyl, aryl, cyclooc-tadiene or pentamethyl cyclopentadiene;
   ii) a composition of the general formula

   $L^2 M^1 R^3$ wherein $L^2$ is either a single cyclic polyolefin or nitrogenous bidentate ligand or a pair of nitrogenous or acetylenic monodentate ligands; $M^1$ is rhodium or iridium; and $R^3$ is cyclooctadiene or pentamethyl cyclopentadiene;
   iii) a composition of the general formula

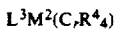
   $L^3 M^2 (C_rR^4_4)$ wherein $L^3$ is either a single cyclic polyolefin or nitrogenous bidentate ligand or a pair of nitrogenous monodentate ligands; $M^2$ is a platinum, palladium, rhodium or iridium; and $R^4$ is $COOR^5$, wherein $R^5$ is hydrogen or alkyl having from 1 to 10 carbons;
   iv) a composition of the general formula

   $L^4 M^3 (COOR^6)_2$ or a dimer thereof, wherein $L^4$ is a non-nitrogenous cyclic polyolefin ligand; $M^3$ is platinum or iridium; and $R^6$ is alkyl;
   v) a composition comprising the reaction product of $L^5 RhX$ and $R^7 MgX$ wherein $L^5$ is a non-nitrogenous cyclic polyolefin ligand; $R^7$ is methyl, benzyl, aryl, cyclooctadiene or pentamethyl cyclopentadiene; and X is a halide, wherein said platinum group metal compound is provided in an amount effective to supply from 0.01 to 1.0 parts per million of platinum group metal per part of fuel.
   vi) palladium acetylene complexes having the general formula

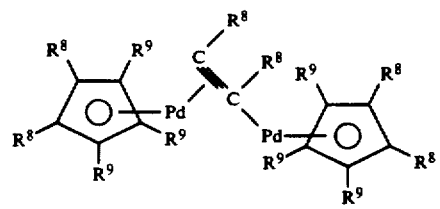

wherein $R^8$ is aryl or alkyl; and $R^9$ is aryl;
   vii) metal allyl complexes having the general formula

   $M^r(C_3H_5)_3$ wherein $M^4$ is rhodium or iridium;
   viii) platinum (IV) compositions having the general formula

   $R^9_3 PtR^{10}$ wherein $R^9$ is aryl, alkyl or mixtures thereof; and $R^{10}$ is hydroxyl, acetylacetonate, cyclopentadiene or pentamethyl cyclopentadiene; and
   ix) a composition of the general formula

   $L^6 M^5 R^{13}$ wherein $L^6$ is substituted or unsubstituted butadiene or cyclohexadiene; $M^5$ is rhodium or iridium; and $R^{13}$ is cyclopentadiene or pentamethyl cyclopentadiene, wherein said composition
   A. is resistant to breakdown under ambient temperatures;
   B. contains no more than about 500 ppm phosphorus, arsenic, antimony or halides; and
   C. has a partition ratio sufficient to maintain preferential solubility in the fuel.

2. The method of claim 1, wherein said injection timing is retarded between about 0.5° and about 8° before top dead center.

3. The method of claim 2, wherein said injection timing is retarded between about 2° and about 6° before top dead center.

4. The method of claim 1, wherein said composition has a breakdown temperature at least about 50° C.

5. The method of claim 1, wherein the partition ratio of said composition is at least about 25.

6. The method of claim 5, wherein said composition has at least one platinum group metal-to-carbon covalent bond.

7. The method of claim 1, wherein $L^1$, $L^2$, and $L^3$ are selected from the group consisting of cyclopentadiene, cyclooctadiene, pentamethyl cyclopentadiene, cyclooctatetrene, o-phenantholine, o-toluidine, norbornadiene, pyridine, and bipyridine.

8. The method of claim 1, wherein $L^4$ and $L^5$ are selected from the group consisting of cyclooctadiene and pentamethyl cyclopentadiene.

9. The method of claim 1, wherein said additive further comprises a fuel-soluble solvent for said composition comprising octyl nitrate.

10. The method of claim 1 which further comprises disposing a diesel engine particulate trap in the exhaust stream of said engine.

11. The method of claim 10, wherein said diesel engine particulate trap is made of ceramic, metal, glass fibers, or mixtures thereof.

12. The method of claim 11, wherein said diesel engine particulate trap further comprises an auxiliary heater to raise the temperature of the diesel engine particulate trap at programmed times in the engine operation cycle.

* * * * *

UNITED STATES PATENT AND TRADEMARK OFFICE
CERTIFICATE OF CORRECTION

PATENT NO. : 5,266,083
DATED : November 30, 1993
INVENTOR(S) : Jeremy D. Peter-Hoblyn, James M. Valentine, W. Robert Epperly, Barry N. Sprague It is certified that error appears in the above-indentified patent and that said Letters Patent is hereby corrected as shown below:

At column 3, line 9, "prior t placing" should read --prior to placing--.

At column 7, line 67, "bis($^5$ pentaphenyl cyclopentadiene)" should read --bis ($\eta^5$-pentaphenyl cyclopentadiene)--.

At column 11, line 37, "cyclooc-tadi-ene" should read --cyclooctadi-ene--.

At column 11, line 50, "$L^3M^2(C_T R^4_4)$" should read --$L^3M^2(C_4 R^4_4)$--.

At column 12, line 21, "$M^T(C_3H_5)_3$" should read --$M^4(C_3H_5)_3$--.

Signed and Sealed this

Sixteenth Day of May, 1995

Attest:

BRUCE LEHMAN

Attesting Officer       Commissioner of Patents and Trademarks